United States Patent
Bolotin et al.

(10) Patent No.: US 8,017,769 B2
(45) Date of Patent: Sep. 13, 2011

(54) COLORLESS WATER-SOLUBLE ORGANIC LUMINOPHORES AND INTERMEDIATES THEREOF

(75) Inventors: Boris Markovich Bolotin, Moscow (RU); Yevgeniy Alexeyevich Birgen, Moscow (RU); Maria Leonardovna Kukushkina, Moscow (RU); Yelena Viktorovna Yakovleva, Moscow (RU)

(73) Assignees: Allami Nyomda Nyrt, Budapest (HU); Boris Markovich Bolotin, Moscow (RU)

( * ) Notice: Subject to any disclaimer, the term of this patent is extended or adjusted under 35 U.S.C. 154(b) by 654 days.

(21) Appl. No.: 12/093,679

(22) PCT Filed: Jul. 26, 2006

(86) PCT No.: PCT/HU2006/000062
§ 371 (c)(1),
(2), (4) Date: May 23, 2008

(87) PCT Pub. No.: WO2007/012905
PCT Pub. Date: Feb. 1, 2007

(65) Prior Publication Data
US 2008/0312436 A1    Dec. 18, 2008

(30) Foreign Application Priority Data
Jul. 28, 2005   (RU) .............................. 2005123869

(51) Int. Cl.
| | |
|---|---|
| C07D 417/12 | (2006.01) |
| C07D 417/14 | (2006.01) |
| C07D 413/12 | (2006.01) |
| C07D 277/66 | (2006.01) |
| C09K 11/06 | (2006.01) |
| C09D 11/00 | (2006.01) |

(52) U.S. Cl. ... 544/194; 544/213; 544/111; 252/301.23; 252/301.28; 252/301.32

(58) Field of Classification Search .................. 544/194, 544/213; 252/301.23, 301.28, 301.32; 262/301.23, 262/301.28, 301.32
See application file for complete search history.

(56) References Cited

U.S. PATENT DOCUMENTS
3,162,642 A   12/1964  McCafferty
3,491,106 A   1/1970   Freyermuth

FOREIGN PATENT DOCUMENTS
EP    1 291 396 A1    3/2003

OTHER PUBLICATIONS

Takamoto et al. Journal of Immunology, 72, 139-147, 1954; CA 48: 25794, 1954, CAPLUS Abstract provided.*
Krasovitskii et al., Orgainic Luminescent Materials, VCH, 1988, pp. 185 to 198.

* cited by examiner

Primary Examiner — Venkataraman Balasubramanian
(74) Attorney, Agent, or Firm — Jason D. Voight

(57) ABSTRACT

Benzazole substituted aminobenzenesulfonate derivatives of formula (A) (wherein X, Q and M are as defined in the specification) are useful as components of water-soluble fluorescent inks and dyes invisible in day-light. Novel intermediates for the above compounds are also disclosed.

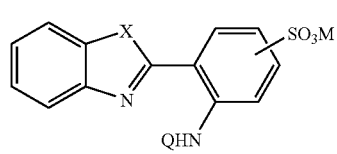

(A)

8 Claims, No Drawings

COLORLESS WATER-SOLUBLE ORGANIC LUMINOPHORES AND INTERMEDIATES THEREOF

This is the National Stage of International Application PCT/HU2006/000062, filed Jul. 26, 2006.

The invention relates to water-soluble fluorescent organic compounds (luminophores), which are colorless under visible light, intermediates thereof and their use as a component of water-soluble fluorescent inks and dyes invisible in daylight, which can be used for manual protection of official, book-keeping and other business documents, and in the field of microbiological research work as well.

The majority of the known water-soluble luminophores, such as sulforhodamine, fluorescein sodium, eosines, acridines, curcumin, riboflavin, erythrosine and the like (EP 1291396 A1) are coloured i.e. absorb light in the visible spectrum and their utilization for safety purposes is limited by this fact (i.e. the absorption of light).

Among the nearly colourless water-soluble luminophores, several water-soluble optical bleachers can be considered as analogs (B. M. Krasovitskii, B. M. Bolotin: Organic luminescent materials, ed. by VCH, 1989, p. 185 to 198). Those bleachers, however, fluoresce only in blue to light blue colour.

Thus, it was desirable to make available novel water-soluble organic luminophores which do not absorb light in the visible spectrum but show fluorescence of various colours from blue to yellow or orange.

The object of the invention was attained by providing novel 2-(2-aminosulfophenyl)benzazole derivatives of formula (A) as defined hereinafter, which are characterized in that they contain both acidic groups converted into salt form to ensure water-solubility and groups capable to form intramolecular NH . . . N hydrogen bonds. Intramolecular hydrogen bonds permit of an abnormally large Stokes shift effect resulting in green, yellow or orange fluorescence of the compound which is colourless i.e. non-absorbent in the visible spectrum.

In one aspect, the invention is directed to a compound of formula (A)

(A)

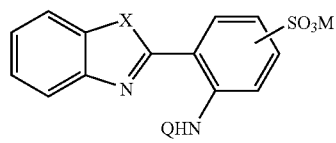

wherein
X is O or S,
Q is

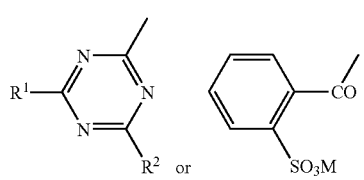

$R^1$ and $R^2$ are each independently

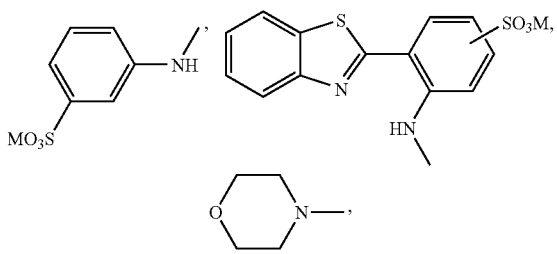

—NHCH$_2$COOM, —N(CH$_2$COOM)$_2$ or Cl,
with the proviso that at least one of $R^1$ and $R^2$ is other than Cl; and
M is Na, K or NH$_4$.

Among the compounds of the invention one group comprises those compounds of formula (A) wherein X is O and Q is

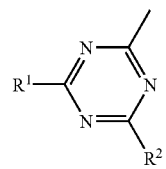

Another group of the compounds of the invention comprises those compounds of formula (A) wherein X is O and Q is

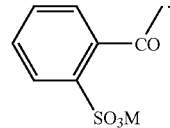

A further group of the compounds of the invention comprises those compounds of formula (A) wherein X is S and Q is

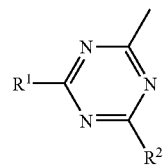

A further group of the compounds of the invention comprises those compounds of formula (A) wherein X is S and Q is

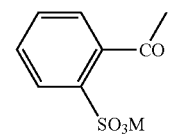

Representative compounds of formula (A) according to the invention include, but not limited to:

disodium salt of 4-[4-Chloro-6-(3-sulfophenylamino)-1,3,5-triazin-2-yl-amino]-3-(benzo[d]thiazol-2-yl)benzenesulfonic acid;

pentapotassium salt of 4-{4,6-bis-[di(carboxymethyl)amino]-1,3,5-triazin-2-yl-amino}-3-(benzo[d]thiazol-2-yl)benzenesulfonic acid;

disodium salt of 4-{4-[2-(benzo[d]thiazol-2-yl)-4-sulfophenylamino]-6-chloro-1,3,5-triazin-2-ylamino}-3-(benzo[d]thiazol-2-yl)benzenesulfonic acid;

disodium salt of 4-{4-[2-(benzo[d]thiazol-2-yl)-4-sulfophenylamino]-6-morpholino-1,3,5-triazin-2-ylamino}-3-(benzo[d]thiazol-2-yl)benzenesulfonic acid;

disodium salt of 4-(2-sulfobenzoylamino)-3-(benzo[d]thiazol-2-yl)benzene-sulfonic acid;

disodium salt of 4-(4-carboxymethylamino-6-chloro-1,3,5-triazin-2-ylamino)-3-(benzo[d]thiazol-2-yl)benzenesulfonic acid;

disodium salt of 4-[4-(3-sulfophenylamino)-6-morpholino-1,3,5-triazin-2-yl -amino]-3-(benzo[d]thiazol-2-yl)benzenesulfonic acid;

trisodium salt of 4-[4,6-bis(carboxymethylamino)-1,3,5-triazin-2-ylamino]-3-(benzo[d]thiazol-2-yl)benzenesulfonic acid;

disodium salt of 4-[4-chloro-6-(3-sulfophenylamino)-1,3,5-triazin-2-ylamino]-3-(benzo[d]oxazol-2-yl)benzene-sulfonic acid; and triammonium salt of 4-{4-chloro-6-[di(carboxymethyl)amino]-1,3,5-triazin-2-yl -amino}-3-(benzo[d]oxazol-2-yl)benzenesulfonic acid.

The luminophor compounds of formula (A) according to the invention can be used as a component of water-soluble fluorescent inks and dyes invisible in daylight e.g. in ink jet printers or pad-inks, moreover for microbiological staining. Thus, in a further aspect, the invention is directed to the use of a compound of the invention for the above purposes.

The compound of formula (A) according to the invention can be prepared by analogous processes well-known for a person skilled in the art, e.g. by using the following reaction sequence:

a) reacting isatoic anhydride with 2-aminophenol or 2-aminothiophenol to obtain a 2-(2-aminophenyl)benzazole (wherein the term "benzazole" means benzoxazole or benzothiazole);

b) sulfonating (2-aminophenyl)benzazole obtained in step a) to obtain an intermediate compound corresponding to a compound of formula (A) wherein X is O or S; Q is H; and M is H;

c) reacting the compound obtained in step b) with cyanuric chloride (i.e. 2,4,6-trichloro-1,3,5-triazine) to obtain an intermediate compound corresponding to a compound of formula (A) wherein X is O or S; Q is 4,6-dichloro-1,3,5-triazin-2-yl; and M is H;

d) replacing at least one of the chloro atoms in the triazine moiety of the compound obtained in step c) with an amine corresponding to any of the amino groups defined above for the meaning of $R^1$ and $R^2$ in formula (A) to give a compound of formula (A) wherein X is O or S; Q is 4-$R^1$-6-$R^2$-1,3,5-triazin-2-yl; and M is H; or e) acylating the compound obtained in step b) with ortho-sulfobenzoic anhydride to give a compound of formula (A) wherein X is O or S; Q is 2-$SO_3$M-benzoyl; and M is H;

and, if required, f) converting an acidic group being present in a compound obtained by any of steps b), c), d) and e) into a sodium, potassium or ammonium salt thereof.

The starting materials and reactants used in the process outlined above are commercially available or described in the prior art literature or can be prepared in a manner known per se.

Intermediate products of steps b), c) and optional step f) of the process outlined above are novel compounds. Preparations of said intermediate compounds are described in detail in the working examples below. Thus, in a further aspect, the invention is directed to a novel intermediate compound of formula (A')

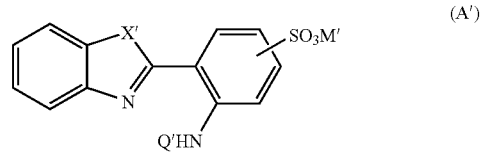

wherein
X' is O or S,
Q' is H or

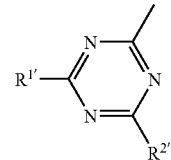

$R^{1'}$ and $R^{2'}$ are simultaneously Cl; and
M' is H, Na, K or $NH_4$.

In the following, examples are given which serve to illustrate the invention.

EXAMPLE 1

4-Amino-3-(benzo[d]thiazol-2-yl)benzenesulfonic acid (Compound I)

2-Aminothiophenol (137.7 g) was heated to 110° C., and isatoic anhydride ($C_8H_5NO_3$, 203.9 g) was added portionwise over a 1 h period while taking care to avoid foaming. Thereafter the temperature was raised to 140° C., and heating was continued for about 2 to 4 h until the starting material 2-aminothiophenol was consumed. The melt was poured into an enamel cuvette and after cooling, the cold material was crushed, then boiled in aqueous NaOH solution (12 g of NaOH solved in 3.5 L of water) for 2 to 3 h. The precipitate was filtered off and the filter cake was washed with cold water until the pale blue fluorescence disappeared in the washings. The precipitate was dried at 80° C. to afford 2-(benzo[d]thiazol-2-yl)phenylamine (200 g). The product was used without further purification in the next stage of preparation.

2-(Benzo[d]thiazol-2-yl)phenylamine (100 g) was added portionwise (5 to 6 g each) to 500 ml of accumulator acid (20% sulfuric acid) with occasional stirring over a 2 h period, and the reaction mixture was stirred until complete dissolution of the solids occurred. The solution was filtered on a glass filter and poured on ice water consisting of 500 g of ice and 500 g of water. After cooling the reactive material to room temperature, the precipitate was filtered, washed with isopropyl alcohol and dried at 80° C. to afford sulfuric acid salt of 2-(benzo[d]thiazol-2-yl)phenylamine (120 g). Total amount of the sulfuric acid salt obtained was heated to 200° C. under a constant pressure of 10 mmHg for 7 to 8 h until the exudation of water ceased. After cooling, water (4 L) was added to the reaction mixture, alkalized to pH 9 to 10 with NaOH, and boiled with activated charcoal for 30 min. The hot solution was filtered. The filtrate was cooled to room temperature and acidified to pH 1 with hydrochloric acid. The yellow precipitate was filtered off and washed with acetone to give Compound I.

Yield: 100 g.

Analysis calculated for $C_{13}H_{10}N_2O_3S_2$: C, 50.97; H, 3.29; N, 9.14. found: C, 51.0; H, 3.3; N, 9.1.

EXAMPLE 2

Sodium salt of 4-(4,6-dichloro-1,3,5-triazin-2-ylamino)-3-(benzo[d]thiazol-2-yl)benzenesulfonic acid (Compound II)

A suspension of Compound I (20 g) in acetone (400 mL) was cooled to 0 to 2° C. while a solution of cyanuric chloride (18.5 g) in acetone (150 mL) and an aqueous 10% solution of $Na_2CO_3$ (100 mL) were added separately from two dropping funnels under stirring over a 1 h period. The mixture was stirred until Compound I was consumed as monitored by thin layer chromatography (TLC; eluent: pyridine/isopropanol/concentrated ammonium hydroxide; 2:2:1). After completion of the reaction, Compound II was filtered off, the filter cake was washed with acetone (100 mL), and dried at room temperature to afford the title compound.

Yield: 35 g. The product is not soluble in water. Green fluorescence.

Analysis calculated for $C_{16}H_8Cl_2N_5NaO_3S_2$: C, 40.35; H, 1.69; N, 14.7. found: C, 40.4; H, 1.7; N, 14.7.

EXAMPLE 3

Disodium salt of 4-[4-Chloro-6-(3-sulfophenylamino)-1,3,5-triazin-2-ylamino]-3-(benzo[d]thiazol-2-yl)benzenesulfonic acid (Compound III)

To a mixture of Compound II from Example 2 (35 g) and water 400 (mL), sodium salt of m-aminobenzenesulfonic acid (15.6 g) was added and the mixture was slowly brought to boil when the precipitate dissolved. After boiling for 3 h, the reaction mixture was cooled to 60° C., activated charcoal (5 g) was added and boiled for 30 min. The hot solution was filtered. After cooling to room temperature, acetone (1 L) was added to the filtrate. The precipitated luminophore was filtered off, the filter cake was washed with acetone, and dried at room temperature. Yield: 52 g. The luminophore highly soluble in water. Green fluorescence.

Analysis calculated for $C_{22}H_{13}ClN_6Na_2O_6S_3$: C, 41.61; H, 2.06; Cl, 5.58; N, 13.23. found: C, 41.5; H, 2.1; Cl, 5.6; N, 13.2.

Compound III is highly soluble in water. The colourless aqueous solution shows yellow fluorescence at a wavelength maximum of 550 nm.

EXAMPLE 4

Pentapotassium salt of 4-{4,6-bis-[di(carboxymethyl)amino]-1,3,5-triazin-2-ylamino}-3-(benzo[d]thiazol-2-yl)benzenesulfonic acid (Compound IV)

A mixture of Compound II (35.7 g), water (500 mL), iminodiacetic acid (25 g) dissolved in water (150 mL) and sodium carbonate (20 g) was brought to boil and boiled for 3 h. The whole sediment dissolved. The reaction mixture was cooled to 60° C., activated charcoal (5 g) was added, and boiled for 30 min. The hot solution was filtered. The filtrate was acidified to pH 1 to 2 with hydrochloric acid, then heated until complete dissolution of the precipitate. The mixture was left at room temperature overnight. The precipitate was filtered off, washed with water, and dried at room temperature to afford the free acid form of Compound IV (38 g).

The free acid form of Compound IV (100 g) was poured into water (500 mL), and potassium carbonate was added portionwise to the mixture until complete dissolution of the solids occurred. Activated charcoal (5 g) was added to the solution, boiled for 10 min, then filtered. The cold filtrate was poured in acetone (1.5 L) while stirring frequently. The precipitate was filtered, washed with acetone, and dried at room temperature.

Yield: 111 g.

Analysis calculated for $C_{27}H_{19}N_4K_5O_{11}S_2$: C, 34.40; H, 1.92; N, 11.70; S, 7.65. found: C, 34.4; H, 1.9; N, 11.7; S, 7.6.

Compound IV is highly soluble in water. The colourless aqueous solution shows yellow fluorescence at a wavelength maximum of 570 nm.

EXAMPLE 5

Disodium salt of 4-{4-[2-(benzo[d]thiazol-2-yl)-4-sulfophenylamino]-6-chloro-1,3,5-triazin-2-ylamino}-3-(benzo[d]thiazol-2-yl)benzenesulfonic acid (Compound V)

To a mixture of Compound I (3.83 g) and Compound II (5 g) water (150 mL) was added, adjusted to pH 8 to 10 with a 10% solution of sodium carbonate, and boiled for 3 h. Meanwhile the pH was kept within the indicated interval by adding more sodium carbonate solution, if necessary. The white precipitate formed was filtered, the filter cake was washed with water, and dried at room temperature.

Yield: 6.1 g.

Compound V shows yellow fluorescence. It is poorly soluble in water.

Analysis calculated for $C_{29}H_{16}ClN_7Na_2O_6S_4$: C, 45.34; H, 2.10; N, 12.76. found: C, 45.4; H, 2.0; N, 12.8.

EXAMPLE 6

Disodium salt of 4-{4-[2-(benzo[d]thiazol-2-yl)-4-sulfophenylamino]-6-morpholino-1,3,5-triazin-2-ylamino}-3-(benzo[d]thiazol-2-yl)benzenesulfonic acid (Compound VI)

A mixture of Compound V (6 g), morpholine (0.73 g) and water (150 mL) was boiled for 3 h while keeping at pH 8 to 10 by addition of a 10% sodium carbonate solution (according to the process of Example 5). After boiling for 30 min, the sediment dissolved. After cooling, the solution was filtered and poured in acetone. The precipitate was filtered, washed with acetone and dried at room temperature.

Yield: 3.5 g.

Analysis calculated for $C_{33}H_{24}N_8Na_2O_7S_4$: C, 48.40; H, 2.95; N, 13.68; S, 15.66. found: C, 48.4; H, 3.0; N, 13.7; S, 15.7.

Compound VI is highly soluble in water. The colourless aqueous solution shows orange-coloured fluorescence at a wavelength maximum of 582 nm.

EXAMPLE 7

Disodium salt of 4-(2-sulfobenzoylamino)-3-(ben-
zoldlthiazol-2-yl)benzenesulfonic acid (Compound
VII)

Compound I (5 g) in water (80 mL) was heated until the precipitate dissolved, then the solution was cooled to 25° C. and sodium acetate (1.85 g) was added, when partial precipitation occurred. To the reactive material ortho-sulfobenzoic anhydride (5.52 g) was immediately added and stirred at room temperature for 3 h until the complete depletion of Compound I was confirmed by thin layer chromatography (TLC). Then activated charcoal was added to the reactive material, boiled for 15 min and filtered. The filtrate was evaporated to dryness in water bath, washed with acetone, dissolved in a small amount of water and precipitated with acetone to obtain a white powder showing yellow fluorescence.

Yield: 3.7 g.

Analysis calculated for $C_{20}H_{12}N_2Na_2O_7S_3$: C, 44.94; H, 2.26; N, 5.24; S, 18.00. found: C, 45.0; H, 2.2; N, 5.3; S, 18.1.
Compound VII is highly soluble in water. The colourless aqueous solution shows yellowish green fluorescence at a wavelength maximum of 547 nm.

EXAMPLE 8

Disodium salt of 4-(4-carboxymethylamino-6-
chloro-1,3,5-triazin-2-ylamino)-3-(benzo[d]thiazol-
2-yl)benzenesulfonic acid (Compound VIII)

Glycine (3.5 g) and sodium carbonate (2.5 g) were dissolved in water (150 mL). To this solution Compound II (20 g) and water (3000 mL) were added. The suspension was slowly warmed to 60° C., while the sediment dissolved. The solution was carefully acidified to pH 1 to 2 with hydrochloric acid. The precipitate was filtered, washed with water, and dried at room temperature to obtain Compound VIII in the form of free acid (4 g).

To the free acid form of Compound VIII (100 g) water (500 mL) was poured and sodium carbonate (40.9 g) was added until the sediment fully dissolved. Activated charcoal was added, boiled for 10 min, and filtered. Acetone (500 mL) was added to the filtrate, and the mixture obtained was poured in acetone (1 L). The precipitate was isolated by filtration, washed with acetone, and dried at room temperature.

Yield: 111 g.

Analysis calculated for $C_{18}H_{11}ClN_6Na_2O_5S_2$: C, 40.27; H, 2.07; N, 15.65. found: C, 40.3; H, 2.0; N, 15.6.
Compound VIII is highly soluble in water. The colourless aqueous solution shows yellowish green fluorescence at a wavelength maximum of 548 nm.

EXAMPLE 9

Disodium salt of 4-[4-(3-sulfophenylamino)-6-mor-
pholino-1,3,5-triazin-2-ylamino]-3-(benzo[d]thiazol-
2-yl)benzenesulfonic acid (Compound IX)

A mixture of Compound III (2 g), morpholine (3 g) and water (60 mL) was brought to boil. The mixture was boiled for 3 h while keeping at pH 8 to 10. After cooling the solution was poured in acetone (1 L). The precipitate was isolated by filtration, washed with acetone and dried at room temperature.

Yield: 0.38 g.

Analysis calculated for $C_{33}H_{24}N_8Na_2O_7S_4$: C, 48.40; H, 2.95; N, 13.68; S, 15.66. found: C, 48.4; H, 3.1; N, 13.6; S, 15.7.
Compound IX is highly soluble in water. The colourless aqueous solution shows yellow fluorescence at a wavelength maximum of 565 nm.

EXAMPLE 10

Trisodium salt of 4-[4,6-bis(carboxymethylamino)-1,
3,5-triazin-2-ylamino]-3-(benzo[d]thiazol-2-yl)ben-
zenesulfonic acid (Compound X)

The title compound was prepared as described for Compound VIII above excepting that a 2-fold amount of glycine was used.

Yield: 110 g.

Analysis calculated for $C_{20}H_{14}N_7Na_3O_7S_2$: C, 40.21; H, 2.36; N, 16.41. found: C, 40.2; H, 2.4; N, 16.5.
Compound X is highly soluble in water. The colourless aqueous solution shows yellow fluorescence at a wavelength maximum of 565 nm.

EXAMPLE 11

4-Amino-3-(benzo[d]oxazol-2-yl)benzenesulfonic
acid (Compound XI)

An intimate mixture of 2-aminophenol (109.13 g) and isatoic anhydride (203.9 g) was heated at 140° C. for 2 to 4 h until the formation of carbon dioxide ceased. Then the mixture was placed under vacuum (at a constant pressure of 50 mmHg) and the heating was continued at 180° C. for 3 to 4 h until the formation of water ceased. The melt was poured into a porcellanic mortar and, after cooling, the cold material was pestled, then boiled in a solution of caustic soda (12 g) in water (3.5 L) for 2 to 3 h. After cooling, the precipitate was isolated by filtration, and washed with cold water until the pale blue fluorescence disappeared in the washings. The precipitate was dried at 80° C. to afford 2-(benzo[d]oxazol-2-yl)phenylamine (180 to 185 g). The product was used without further purification in the next stage of preparation.

Ground 2-(benzo[d]oxazol-2-yl)phenylamine (100 g) was added portionwise (5 to 6 g each) to 500 ml of accumulator acid (20% sulfuric acid) with occasional stirring over a 2 h period, and the reaction mixture was stirred until the complete dissolution of the solids occurred. The solution was filtered on a glass filter and poured on ice water consisting of 500 g of ice and 500 g of water. After cooling the reactive material to room temperature, the precipitate was filtered, washed with isopropyl alcohol and dried at 80° C. to afford sulfuric acid salt of 2-(benzo[d]oxazol-2-yl)phenylamine (110 g). The total amount of the sulfuric acid salt obtained was heated at 200° C. under constant pressure of 50 mmHg for 7 to 8 h until the exudation of water ceased. After cooling, the reaction product was suspended in water (4 L), adjusted to pH 9 to 10 with caustic soda, and boiled with activated charcoal for 30 min. The hot solution was filtered. The filter cake was washed with hot water (500 mL). The combined filtrates were cooled to room temperature, then acidified to pH 1 with hydrochloric acid. The yellow precipitate was filtered off, washed with acetone, and dried at room temperature to give Compound XI.

Yield: 90 g.

Analysis calculated for $C_{13}H_{10}N_2O_4S$: C, 53.79; H, 3.47; N, 9.65; S, 11.05. found: C, 53.8; H, 3.5; N, 9.6; S, 11.0.

EXAMPLE 12

Sodium salt of 4-(4,6-dichloro-1,3,5-triazin-2-ylamino)-3-(benzo[d]oxazol-2-yl)benzenesulfonic acid (Compound XII)

The title compound was prepared as described for Compound II above excepting that Compound XI (19.6 g) was used instead of Compound I.

Yield: 32 g.

Analysis calculated for $C_{16}H_8Cl_2N_5NaO_4S$: C, 41.76; H, 1.75; N, 15.22. found: C, 41.8; H, 1.7; N, 15.2.

EXAMPLE 13

Disodium salt of 4-[4-chloro-6-(3-sulfophenylamino)-1,3,5-triazin-2-ylamino]-3-(benzo[d]oxazol-2-yl)benzenesulfonic acid (Compound XIII)

A mixture of Compound XII (1 g), metanilic acid (0.43 g), water (50 mL) and 10% sodium carbonate solution (5 mL) was warmed at 40 to 45° C. for 4 h until complete dissolution of the components occurred. The hot solution was filtered. The filtrate was acidified to pH 1 with hydrochloric acid. The precipitate was isolated by filtration, washed with water, and added to water (25 mL). The mixture was adjusted to pH 8.0 to 8.5 with sodium carbonate, filtered, and the filtrate was diluted with isopropyl alcohol (200 mL). The precipitate was filtered off, and dried at 80° C. to afford Compound XIII.

Yield: 1 g.

Analysis calculated for $C_{22}H_{13}ClN_6Na_2O_7S_2$: C, 42.69; H, 2.12; N, 13.58. found: C, 42.7; H, 2.1; N, 13.6.

Compound XIII is highly soluble in water. The colourless aqueous solution shows green fluorescence at a wavelength maximum of 517 nm.

EXAMPLE 14

Triammonium salt of 4-{4-chloro-6-[di(carboxymethyl)amino]-1,3,5-triazin-2-ylamino}-3-(benzo[d]oxazol-2-yl)benzenesulfonic acid (Compound XIV)

A mixture of Compound XII (1.5 g), iminodiacetic acid (0.435 g), water (75 mL) and 10% sodium carbonate solution (10 mL) was warmed at 40 to 45° C. for 4 h until all components completely dissolved. The hot solution was filtered. The filtrate was acidified to pH 1 with hydrochloric acid. The precipitate was filtered off, washed with water, and transferred in water (40 mL). The mixture was adjusted to pH 8.0 to 8.5 with a 25% ammonium hydroxide solution. The solution was filtered. The filtrate was poured into isopropyl alcohol (300 ml). The precipitate was isolated by filtration, and dried at 80° C. to afford Compound XIV.

Yield: 1.3 g.

Analysis calculated for $C_{20}H_{24}ClN_9O_8S$: C, 40.99; H, 4.13; N, 21.51. found: C, 41.0; H, 4.1; N, 21.4.

Compound XIV is highly soluble in water. The colourless aqueous solution shows green fluorescence at a wavelength maximum of 517 mm.

The invention claimed is:

1. A compound of formula (A)

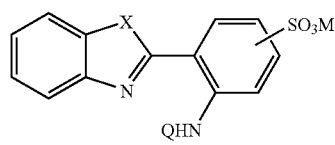
(A)

wherein
X is O or S,
Q is

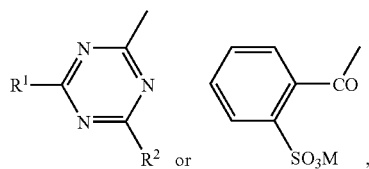

$R^1$ and $R^2$ are each independently

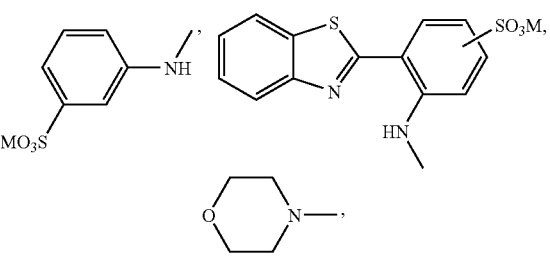

—NHCH$_2$COOM, —N(CH$_2$COOM)$_2$ or Cl,
with the proviso that at least one of $R^1$ and $R^2$ is other than Cl;
and
M is Na, K or NH$_4$.

2. The compound of claim 1 wherein X is O and Q is

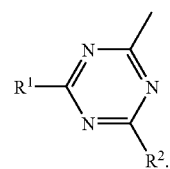

3. The compound of claim 1 wherein X is S and Q is

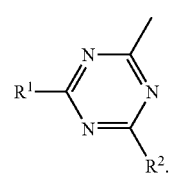

4. The compound of claim 1 which is selected from the group consisting of:
disodium salt of 4-[4-chloro-6-(3-sulfophenylamino)-1,3,5-triazin-2-ylamino]-3-(benzo[d]thiazol-2-yl)benzenesulfonic acid;

pentapotassium salt of 4-{4,6-bis-[di(carboxymethyl)amino]-1,3,5-triazin-2-ylamino}-3-(benzo[d]thiazol-2-yl)benzenesulfonic acid;
disodium salt of 4-{4-[2-(benzo[d]thiazol-2-yl)-4-sulfophenylamino]-6-chloro-1,3,5-triazin-2-ylamino}-3-(benzo[d]thiazol-2-yl)benzenesulfonic acid;
disodium salt of 4-{4-[2-(benzo[d]thiazol-2-yl)-4-sulfophenylamino]-6-morpholino-1,3,5-triazin-2-ylamino}-3-(benzo[d]thiazol-2-yl)benzenesulfonic acid;
disodium salt of 4-(4-carboxymethylamino-6-chloro-1,3,5-triazin-2-ylamino)-3-(benzo[d]thiazol-2-yl)benzenesulfonic acid;
disodium salt of 4-[4-(3-sulfophenylamino)-6-morpholino-1,3,5-triazin-2-ylamino]-3-(benzo[d]thiazol-2-yl)benzenesulfonic acid;
trisodium salt of 4-[4,6-bis(carboxymethylamino)-1,3,5-triazin-2-ylamino]-3-(benzo[d]-thiazol-2-yl)benzenesulfonic acid;
disodium salt of 4-[4-chloro-6-(3-sulfophenylamino)-1,3,5-triazin-2-ylamino]-3-(benzo[d]oxazol-2-yl)benzenesulfonic acid; and
triammonium salt of 4-{4-chloro-6-[di(carboxymethyl)amino]-1,3,5-triazin-2-yl-amino}-3-(benzo[d]oxazol-2-yl)benzenesulfonic acid.

5. A water-soluble luminophore colorless under visible light, a water-soluble fluorescent ink, a water-soluble dye invisible in daylight, or a microbiological stain, said luminophore, ink, dye, or stain comprising the compound of claim 1.

6. A compound of the formula (A')

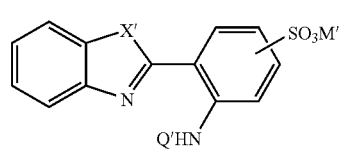

(A')

wherein
X' is O or S,
Q' is

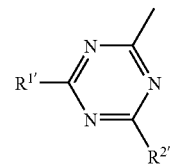

$R^{1'}$ and $R^{2'}$ are simultaneously Cl; and
M' is H, Na, K or $NH_4$.

7. The compound of claim 6, wherein X' is O.

8. The compound of claim 6, wherein M' is Na, K or $NH_4$.

\* \* \* \* \*